United States Patent
Blondino et al.

(10) Patent No.: US 7,410,635 B2
(45) Date of Patent: *Aug. 12, 2008

(54) AEROSOL FORMULATIONS AND AEROSOL DELIVERY OF SCOPOLAMINE

(75) Inventors: Frank E. Blondino, Easton, PA (US); Justin Poklis, Richmond, VA (US); Matthew Baker, Richmond, VA (US)

(73) Assignee: Philip Morris USA Inc., Richmond, VA (US)

(*) Notice: Subject to any disclaimer, the term of this patent is extended or adjusted under 35 U.S.C. 154(b) by 91 days.

This patent is subject to a terminal disclaimer.

(21) Appl. No.: 10/958,329

(22) Filed: Oct. 6, 2004

(65) Prior Publication Data

US 2005/0079137 A1    Apr. 14, 2005

Related U.S. Application Data

(60) Provisional application No. 60/508,875, filed on Oct. 7, 2003.

(51) Int. Cl.
*A61K 9/12* (2006.01)
*A61M 16/00* (2006.01)
*A61M 16/12* (2006.01)

(52) U.S. Cl. ............... 424/45; 514/958; 128/200.14; 128/203.12; 128/203.16

(58) Field of Classification Search ............ 424/45; 514/958; 128/200.14, 203.12, 203.16
See application file for complete search history.

(56) References Cited

U.S. PATENT DOCUMENTS

| | | | |
|---|---|---|---|
| 5,743,251 A | 4/1998 | Howell et al. | |
| 6,234,167 B1 | 5/2001 | Cox et al. | |
| 6,501,052 B2 * | 12/2002 | Cox et al. | 219/486 |
| 6,516,796 B1 | 2/2003 | Cox et al. | 128/200.23 |
| 6,557,552 B1 * | 5/2003 | Cox et al. | 128/203.27 |
| 6,568,390 B2 | 5/2003 | Nichols et al. | |
| 6,640,050 B2 | 10/2003 | Nichols et al. | |
| 6,682,716 B2 * | 1/2004 | Hodges et al. | 424/45 |
| 6,701,922 B2 * | 3/2004 | Hindle et al. | 128/203.27 |
| 6,766,220 B2 * | 7/2004 | McRae et al. | 700/266 |
| 6,799,572 B2 * | 10/2004 | Nichols et al. | 128/203.26 |
| 6,854,461 B2 * | 2/2005 | Nichols et al. | 128/203.16 |
| 6,883,516 B2 * | 4/2005 | Hindle et al. | 128/200.14 |
| 6,923,179 B2 * | 8/2005 | Gupta et al. | 128/203.17 |
| 7,040,314 B2 * | 5/2006 | Nguyen et al. | 128/203.12 |
| 7,077,130 B2 * | 7/2006 | Nichols et al. | 128/203.26 |
| 7,117,867 B2 * | 10/2006 | Cox et al. | 128/200.14 |
| 7,128,067 B2 * | 10/2006 | Byron et al. | 128/200.14 |
| 7,147,170 B2 * | 12/2006 | Nguyen et al. | 239/13 |
| 7,163,014 B2 * | 1/2007 | Nichols et al. | 128/203.26 |
| 7,167,776 B2 * | 1/2007 | Maharajh et al. | 700/266 |
| 7,173,222 B2 * | 2/2007 | Cox et al. | 219/486 |
| 2003/0106551 A1 | 6/2003 | Sprinkel, Jr. et al. | |
| 2004/0009128 A1 * | 1/2004 | Rabinowitz et al. | 424/46 |
| 2004/0016427 A1 * | 1/2004 | Byron et al. | 128/200.14 |
| 2004/0079368 A1 * | 4/2004 | Gupta et al. | 128/203.12 |
| 2004/0081624 A1 * | 4/2004 | Nguyen et al. | 424/44 |
| 2004/0129793 A1 * | 7/2004 | Nguyen et al. | 239/13 |
| 2004/0151670 A1 * | 8/2004 | Blondino et al. | 424/45 |
| 2004/0170405 A1 * | 9/2004 | Sherwood et al. | 392/397 |
| 2004/0223917 A1 * | 11/2004 | Hindle et al. | 424/45 |
| 2004/0223918 A1 * | 11/2004 | Pham et al. | 424/45 |
| 2005/0126624 A1 * | 6/2005 | Pellizzari | 136/253 |
| 2005/0133029 A1 * | 6/2005 | Nichols et al. | 128/203.26 |
| 2005/0143866 A1 * | 6/2005 | McRae et al. | 700/299 |
| 2005/0205084 A1 * | 9/2005 | Gupta et al. | 128/200.14 |

FOREIGN PATENT DOCUMENTS

| | | |
|---|---|---|
| DE | 3926751 A1 | 2/1991 |
| EP | 1177793 A | 2/2002 |
| WO | WO 86/04233 A | 7/1986 |
| WO | WO 99/16417 A | 4/1999 |
| WO | WO 01/62227 A | 8/2001 |
| WO | WO 01/81182 A | 11/2001 |
| WO | WO 02/094237 A | 11/2002 |

OTHER PUBLICATIONS

International Search Report and Written Opinion dated Oct. 25, 2005 for PCT/US2004/032449.
International Preliminary Report on Patentability dated Apr. 10, 2006 for PCT/US2004/032449.

* cited by examiner

*Primary Examiner*—Mina Haghighatian
(74) *Attorney, Agent, or Firm*—Buchanan Ingersoll & Rooney PC

(57) ABSTRACT

A liquid aerosol formulation comprising at least one thermally stable active ingredient selected from the group consisting of butalbital, lorazepam, ipratropium, baclofen, morphine, scopolamine, pharmaceutically acceptable salts and esters thereof and derivatives thereof. The liquid formulation can include an organic solvent such as propylene glycol and one or more optional excipients. The active ingredient can be present in an amount of 0.01 to 5 weight percent and the formulation can be heated to provide a vapor which forms an aerosol having a mass median aerodynamic diameter of less than 3 μm.

11 Claims, No Drawings

AEROSOL FORMULATIONS AND AEROSOL DELIVERY OF SCOPOLAMINE

This application claims the benefit of U.S. Provisional Application No. 60/508,875 entitled AEROSOL FORMULATIONS AND AEROSOL DELIVERY OF BUTALBITAL, LORAZEPAM, IPRATROPIUM, BACLOFEN, MORPHINE AND SCOPOLAMINE, filed on Oct. 7, 2003, the entire contents of which is hereby incorporated by reference

FIELD OF THE INVENTION

The invention relates generally to an liquid aerosol formulation. More specifically, the invention relates to a liquid aerosol formulation comprising at least one thermally stable active ingredient selected from the group consisting of butalbital, lorazepam, ipratropium, baclofen, morphine, scopolamine, pharmaceutically acceptable salts and esters thereof and derivatives thereof. The invention further relates to aerosol generating devices and methods for generating aerosols.

BACKGROUND

Aerosols are gaseous suspensions of fine solid or liquid particles. Aerosols are useful in a wide variety of applications. For example, medicated liquids may be administered in aerosol form. Medicated aerosols include materials that are useful in the treatment of respiratory ailments. In such applications, the aerosols may be produced by an aerosol generator and inhaled into a patient's lungs.

Aerosol generators are known that include a heated tube for vaporizing liquid. For example, commonly assigned U.S. Pat. No. 5,743,251, which is incorporated herein by reference in its entirety, discloses an aerosol generator including a tube and a heater operable to heat the tube to a sufficient temperature to volatilize liquid in the tube. It is disclosed that the volatilized material expands out of an end of the tube and admixes with ambient air, thereby forming an aerosol.

Other aerosol generators including a heated tube for vaporizing liquids to produce an aerosol are described in commonly-assigned U.S. Pat. Nos. 6,234,167 and 6,568,390 and U.S. patent application Ser. No. 10/003,437 filed Dec. 6, 2001 and U.S. Provisional Application No. 60/408,894, filed Sep. 6, 2002, each being incorporated herein by reference in its entirety.

SUMMARY

One embodiment provides a liquid aerosol formulation comprising at least one thermally stable active ingredient selected from the group consisting of butalbital, lorazepam, ipratropium, baclofen, morphine, scopolamine, pharmaceutically acceptable salts and esters thereof and derivatives thereof. The formulation may contain any desired amount of the active ingredient. In a preferred embodiment, the formulation may contain 0.01 to 5% by weight of the thermally stable active ingredient.

The liquid aerosol formulation may further comprise an organic solvent. The organic solvent may be, but is not limited to, a short chain ($C_1$-$C_6$) alcohol. The short chain ($C_1$-$C_6$) alcohol may be, but is not limited to, glycerin, ethylene glycol, diethylene glycol, propylene glycol, n-propyl alcohol, isopropyl alcohol, butanol, ethanol, sorbitol, dipropylene glycol, tripropylene glycol, and hexylene glycol. Preferably, the organic solvent is propylene glycol or dipropylene glycol.

The liquid aerosol formulation may further comprise at least one pharmaceutically acceptable excipient. The excipient may be, but is not limited to, antioxidants, stabilizing agents, flavoring agents, solubilizers, cosolvents, preservatives and combinations thereof. Preferably, the cosolvent is ethanol, water, glycerol and/or diethyl ether. Preferably, the solubilizer is ethanol, isopropanol, butanol, benzyl alcohol, ethylene glycol, butanediols and isomers thereof, glycerol, pentaerythritol, sorbitol, mannitol, transcutol, dimethyl isosorbide, polyethylene glycol, polypropylene glycol, polyvinylalcohol, hydroxypropyl methylcellulose and other cellulose derivatives, cyclodextrins and cyclodextrin derivatives, and/or mixtures thereof.

In a preferred embodiment, the thermally stable active ingredient comprises butalbital and the organic solvent is propylene glycol.

In a preferred embodiment, the thermally stable active ingredient comprises lorazepam and the organic solvent is propylene glycol.

In a preferred embodiment, the thermally stable active ingredient comprises ipratropium and the organic solvent is propylene glycol.

In a preferred embodiment, the thermally stable active ingredient comprises baclofen and the organic solvent is propylene glycol.

In a preferred embodiment, the thermally stable active ingredient comprises morphine and the organic solvent is propylene glycol.

In a preferred embodiment, the thermally stable active ingredient comprises scopolamine and the organic solvent is propylene glycol.

According to one embodiment, a method of generating an aerosol comprises supplying a liquid aerosol formulation to a flow passage, heating the liquid aerosol formulation in the flow passage so as to volatilize a liquid component thereof and form a vapor which exits from an outlet of the flow passage, and contacting the vapor with a gaseous medium so as to form an aerosol, wherein the liquid aerosol formulation includes at least one thermally stable active ingredient selected from the group consisting of butalbital, lorazepam, ipratropium, baclofen, morphine, scopolamine, pharmaceutically acceptable salts and esters thereof. For drug delivery, the liquid aerosol formulation preferably comprises particles of propylene glycol having a mass median aerodynamic diameter (MMAD) of less than 3 µm. The liquid aerosol formulation may further include at least one thermally stable active ingredient and the aerosol comprises particles of the thermally stable active ingredient having an MMAD of less than 3 µm.

In a preferred embodiment, the thermally stable active ingredient comprises butalbital and the aerosol comprises butalbital particles having an MMAD of less than 3 µm.

In a preferred embodiment, the thermally stable active ingredient comprises lorazepam and the aerosol comprises lorazepam particles having an MMAD of less than 3 µm.

In a preferred embodiment, the thermally stable active ingredient comprises ipratropium and the aerosol comprises ipratropium particles having an MMAD of less than 3 µm.

In a preferred embodiment, the thermally stable active ingredient comprises baclofen and the aerosol comprises baclofen particles having an MMAD of less than 3 µm.

In a preferred embodiment, the thermally stable active ingredient comprises morphine and the aerosol comprises morphine particles having an MMAD of less than 3 µm.

In a preferred embodiment, the thermally stable active ingredient comprises scopolamine and the aerosol comprises scopolamine particles having an MMAD of less than 3 µm.

In a preferred embodiment, the flow passage is a capillary sized flow passage and the aerosol is formed in a mouthpiece of a handheld inhaler. The aerosol may include particles of the thermally stable active ingredient having an MMAD of 0.1 to 2.5 μm and the aerosol preferably has a recovery rate of at least 90% during generation of the aerosol. Preferably, the flow passage is heated by a resistance heater located in a handheld inhaler, the inhaler including a power supply and control electronics which controls supply of electrical power to the heater as a function of a resistance target in a range of 0.5 to 1 ohm.

According to one embodiment, an aerosol generator comprises a flow passage adapted to receive a liquid aerosol formulation from a liquid supply, the liquid aerosol formulation comprising at least one thermally stable active ingredient selected from the group consisting of butalbital, lorazepam, ipratropium, baclofen, morphine, scopolamine, pharmaceutically acceptable salts and esters thereof and derivatives thereof, and a heater operable to heat the liquid formulation in at least a portion of the flow passage sufficiently to vaporize the liquid formulation and generate an aerosol containing the active ingredient. The aerosol generator may comprise a hand-held inhaler having a mouthpiece, the flow passage comprising a capillary sized flow passage having an outlet in fluid communication with an interior of the mouthpiece. In a preferred embodiment, the heater is a resistance heater comprising a section of a metal capillary tube and the flow passage comprises the interior of the metal capillary tube. The aerosol generator may comprise a hand-held inhaler having a power supply and control electronics which controls supply of electrical power to the heater as a function of a control parameter selected to achieve boiling of the liquid formulation in the flow passage. The liquid supply may comprise a reservoir containing the liquid formulation under a pressure of no greater than about atmospheric pressure.

4. DETAILED DESCRIPTION

Liquid aerosol formulations, aerosol generating devices and methods for generating aerosols are provided.

The liquid aerosol formulations can provide aerosols having selected compositions and controlled particle sizes. The liquid aerosol formulations are suitable for different applications including systemic delivery of medicaments. For example, for drug delivery applications via inhalation, the formulations comprise aerosols having a desirable mass median aerodynamic diameter (MMAD) for targeted delivery. For pulmonary delivery, particles of smaller size are desired than for tracheobronchial delivery or delivery to the oropharynx or mouth. In preferred embodiments, the aerosols have a controlled particle size that is effective to achieve pulmonary delivery of drug formulations.

The liquid aerosol formulation preferably includes an organic solvent and at least one thermally stable active ingredient. The thermally stable active ingredients may be selected from the group consisting of butalbital, lorazepam, ipratropium, baclofen, morphine, scopolamine, pharmaceutically acceptable salts and esters thereof and derivatives thereof. The thermally stable active ingredients can be somewhat or completely soluble in the liquid aerosol formulation. In addition, the liquid aerosol formulation is preferably propellant free.

Butalbital, lorazepam, ipratropium, baclofen, morphine, scopolamine, pharmaceutically acceptable salts and esters thereof and derivatives thereof are sufficiently soluble in an organic solvent to form solutions at ambient conditions. The concentration of butalbital, lorazepam, ipratropium, baclofen, morphine, scopolamine, pharmaceutically acceptable salts and esters in the solution can be varied to control the amount of the active ingredient in such aerosols.

The liquid aerosol formulation may further comprise additional active ingredients, in combination with butalbital, lorazepam, ipratropium, baclofen, morphine, scopolamine, pharmaceutically acceptable salts and esters thereof and/or derivatives thereof.

The liquid aerosol formulation may further comprise an organic solvent. Examples of organic solvents include, but are not limited to, short chain ($C_1$-$C_6$) alcohols, such as n-propyl alcohol, isopropyl alcohol, butanol, ethanol, glycerin, ethylene glycol, diethylene glycol, propylene glycol, sorbitol, dipropylene glycol, tripropylene glycol, and hexylene glycol. Preferred short chain alcohols are propylene glycol and dipropylene glycol. Propylene glycol (PG) is especially preferred.

The liquid aerosol formulation may also include any pharmaceutically acceptable excipient. Such excipients may include, but are not limited to, antioxidants, stabilizing agents, flavoring agents, solubilizers, cosolvents, preservatives and combinations thereof.

Preferably, the cosolvent is ethanol, water, glycerol and diethyl ether. Preferably, the solubilizer is ethanol, isopropanol, butanol, benzyl alcohol, ethylene glycol, butanediols and isomers thereof, glycerol, pentaerythritol, sorbitol, mannitol, transcutol, dimethyl isosorbide, polyethylene glycol, polypropylene glycol, polyvinylalcohol, hydroxypropyl methylcellulose and other cellulose derivatives, cyclodextrins and cyclodextrin derivatives or mixtures thereof.

In a preferred embodiment, the liquid aerosol formulation is flowed through a capillary sized flow passage in which the liquid is heated to a sufficiently high temperature to vaporize the liquid. The vapor exits the flow passage and admixes with gas, preferably ambient air, to produce an aerosol which is inhaled by a user. The size of the aerosol particles thus produced can be controlled for delivery to the lung.

The capillary passage can have different transverse cross-sectional shapes, such as round, oval, triangular, square, rectangular, other polygonal shapes, or the like, as well as other non-geometric shapes. Different portions of the capillary passage can have different cross-sectional shapes. As described below, the size of the capillary passage can be defined by its transverse cross-sectional area. For a capillary passage having a round cross-section, the size of the flow passage may be defined by its diameter. Alternatively, the capillary passage may be non-circular in cross section and the size of the capillary passage may be defined by its width. For example, the capillary passage can have a maximum width of 0.01 to 10 mm, preferably 0.05 to 1 mm, and more preferably 0.1 to 0.5 mm. Alternatively, the capillary passage can be defined by its transverse cross sectional area, which can be $8 \times 10^{-5}$ to 80 $mm^2$, preferably $2 \times 10^{-3}$ to $8 \times 10^{-1}$ $mm^2$, and more preferably $8 \times 10^{-3}$ to $2 \times 10^{-1}$ $mm^2$.

Details of an aerosol generator which can be used to aerosolize the liquid formulation are described in commonly assigned U.S. Pat. Nos. 5,743,251; 6,234,167; 6,516,796; and 6,568,390, the entire disclosures of which are hereby incorporated by reference. Other suitable aerosol generators are described in commonly assigned U.S. patent application Ser. No. 10/341,521 filed Jan. 14, 2003, the entire disclosure of which is hereby incorporated by reference. Control schemes for heating the flow passage are described in commonly assigned U.S. Pat. No. 6,501,052, the entire disclosure of which is hereby incorporated by reference, and in commonly assigned U.S. patent application Ser. No. 10/206,320 filed Jul. 29, 2002, the entire disclosure of which is hereby incorporated by reference.

As described in commonly-assigned U.S. Provisional Patent Application No. 60/408,295, filed Sep. 6, 2002, which is incorporated herein by reference in its entirety, embodiments of the capillary passage can comprise an outlet section, which controls the velocity of vapor exiting the outlet end of the capillary passage, i.e, the exit velocity of the vapor, so as to control the particle size of aerosol generated by the aerosol generating device.

The material forming the capillary passage can be any suitable material, including metals, plastics, polymers, ceramics, glasses, or combinations of these materials. Preferably, the material is a heat-resistant material capable of withstanding the temperatures and pressures generated in the capillary passage, and also resisting the repeated heating cycles utilized to generate multiple doses of aerosols. In addition, the material forming the capillary passage preferably is non-reactive with the liquid that is aerosolized.

In another alternative embodiment, the capillary passage can be formed in a polymer, glass, metal and/or ceramic monolithic or multilayer (laminated) structure (not shown). Suitable ceramic materials for forming the capillary passage include, but are not limited to, alumina, zirconia, silica, aluminum silicate, titania, yttria-stabilized zirconia, or mixtures thereof. A capillary passage can be formed in the monolithic or multilayer body by any suitable technique, including, for example, machining, molding, extrusion, or the like.

In embodiments, the capillary passage can have a length from 0.5 to 10 cm, and preferably from 1 to 4 cm.

The liquid aerosol formulation supplied from a liquid source is heated in the capillary passage to form a vapor during operation of the aerosol generating device. In a preferred embodiment, the capillary comprises metal tubing heated by passing an electrical current along a length of the capillary tubing via a first electrode and a second electrode. However, as described above, the capillary passage can have other alternative constructions, such as a monolithic or multilayer construction, which include a heater such as a resistance heating material positioned to heat the fluid in the capillary passage. For example, the resistance heating material can be disposed inside of, or exterior to, the capillary passage.

The capillary passage may comprise an electrically conductive tube provided with a downstream electrode and an upstream electrode. In this embodiment, the capillary is a controlled temperature profile (CTP) construction, such as disclosed in copending and commonly assigned U.S. application Ser. No. 09/957,026, filed Sep. 21, 2001, which is incorporated herein by reference in its entirety. In the controlled temperature profile capillary, the downstream electrode has an electrical resistance sufficient to cause it to be heated during operation of the aerosol generating device, thereby minimizing heat loss at the outlet end of the capillary tube.

The tube forming the capillary passage can be made entirely of stainless steel or any other suitable electrically conductive materials. Alternatively, the tube can be made of a non-conductive or semi-conductive material incorporating a heater made from an electrically conductive material, such as platinum. Electrodes connected at spaced positions along the length of the tube or heater define a heated region between the electrodes. A voltage applied between the two electrodes generates heat in the heated region of the capillary passage based on the resistivity of the material(s) making up the tube or heater, and other parameters such as the cross-sectional area and length of the heated region section. As the fluid flows through the capillary passage into the heated region between the first and second electrodes, the fluid is heated and converted to a vapor. The vapor passes from the heated region of the capillary passage and exits from the outlet end. In some preferred embodiments, the volatilized fluid is entrained in ambient air as the volatilized fluid exits from the outlet, causing the volatilized fluid to condense into small droplets and form a condensation aerosol. In a preferred embodiment, the MMAD of the droplet size is 0.1 to 2.5 µm.

The temperature of the liquid in the capillary passage can be calculated based on the measured or calculated resistance of the heating element. For example, the heating element can be a portion of a metal tube, or alternatively a strip or coil of resistance heating material. Control electronics can be used to regulate the temperature of the capillary passage by monitoring the resistance of the heater. For example, the control electronics can control the temperature profile of the capillary passage during operation of the aerosol generating device. The control electronics can also control the output of the display. The display is preferably a liquid crystal display (LCD). The display can depict selected information pertaining to the condition or operation of the aerosol generating device. The control electronics can also control the operation of one or more valves during operation of the aerosol generating device; monitor the initial pressure drop caused by inhalation and sensed by the pressure sensor; and monitor the condition of the battery unit that provides electrical power to components of the aerosol generating device.

Preferably, the aerosol particles have a MMAD between about 0.1 µm and about 2.5 µm. As described above, the aerosol generating device can provide aerosols having a controlled particle size, including aerosols sized for the targeted delivery of drugs to the lung. These aerosols offer a number of advantages for delivering drugs to the deep lung. For example, mouth and throat deposition are minimized, while deposition in the deep lung is maximized, especially when combined with a breath hold. Moreover, when using a suitable hydrophilic carrier, deposition may be further enhanced by hygroscopic growth.

The aerosol generating device preferably generates aerosols in which 95% of the aerosol particles (aerosol droplets) have a size in the range between about 0.1 µm to about 2.5 µm. The aerosol generating device preferably incorporates a processor chip for controlling the generation process. The processor, with suitable sensors, also triggers the aerosol generation at any desired time during an inhalation. The drug to be aerosolized is provided with a carrier. By the choice of suitable hydrophilic carriers, the aerosol generating device can take advantage of hygroscopic growth in the respiratory system.

Operation of the preferred aerosol generating device for delivering aerosolized thermally stable active ingredients is as follows. First, a liquid aerosol formulation including at least one thermally stable active ingredient is delivered to the heated capillary passage. The liquid vaporizes in the capillary passage and exits as a vapor jet from the open end of the capillary passage. The vapor jet entrains and mixes with ambient air, and forms a highly concentrated, fine aerosol. As described above, application of heat to vaporize the liquid is typically achieved by resistive heating from passing an electric current through the heater. The applied power is adjusted to maximize the conversion of the fluid into a vapor.

As will be appreciated, the aerosol generating device is capable of controlled vaporization and aerosol formation of drug formulations. The aerosol generating device can provide immediate delivery of aerosol to a patient, thereby not wasting lung capacity, which may be limited due to the health of the patient. Also, the aerosol generating device can provide consistent delivery of controlled amounts of drug formulation to a patient. In addition, in preferred embodiments, the aerosol generated by the aerosol generating device including a capillary passage is only slightly affected by relative humidity and temperature.

EXAMPLES

Example 1

Butalbital Aerosol

An aerosol was generated using butalbital (5-(2-Methylpropyl)-5-(2-propenyl)-2,4,6(1H,3H,5H)-pyrimidinetrione; 5-allyl-5-isobutylbarituric acid) dissolved in propylene glycol (PG).

Experiments were performed to determine if a chemically stable 0.5 μl butalbital (BAR) aerosol could be generated using a 28 gauge, 44 mm long steel capillary using a flow rate of 5 mg/second. A 0.2% butalbital solution in PG was prepared as the formulation to be tested. The aerosol particle size was determined, and chemical stability of butalbital in the generated aerosol was evaluated. Butalbital was purchased from Sigma Aldrich Chemical Co. Propylene glycol was purchased from Dow Chemical Co.

Forced Degradation Studies

Butalbital was subjected to heating with a differential scanning calorimeter. Conditions were optimized to produce total thermal degradation products by heating to 300 degrees Celsius.

Dose Capture and Degradation Determinations

Dose capture determinations were conducted (Table 1). The investigations indicated that an energy of greater than about 74 J was required to aerosolize butalbital and minimize throat deposition. Analysis of samples in PG (pH about 8) indicated a bathochromic shift indicating partial ionization of the compound. 0.1% ascorbic acid was added to acidify the PG (pH about 3) to prevent ionization and the bathochromic shift. Although the shift represents ionization and not true decomposition of the compound, ascorbic acid was added to prevent potential interaction of the partially ionized compound that may represent instability in solution. The bathochromic shift was observed when butalbital was analyzed as a sham and after aerosolization, indicating a relatively stable moiety. The addition of ascorbic acid resulted in the non-ionized form of butalbital before and after aerosolization, as indicated by UV analysis. Using these parameters, with ascorbic acid added to the formulation (Table 1, runs 10-14), an average of 92% was aerosolized and collected. Analysis of the samples from runs 1-8 (Table 1) indicated a low recovery because of the shift in UV spectrum. The average degradation of runs 10-14 was 1.2%.

Particle Size Determinations

After determining energy requirements for aerosolizing butalbital, particle size determinations were performed (Table 2). At energies of approximately 73 J (runs 6-10), a small percentage, less than about 4%, of the recovered butalbital was found on the throat. These parameters and formulations produced aerosols having an average mass median aerodynamic diameter of approximately 0.36 microns. The average recovery for these experiments was approximately 97%.

Based upon the reproducible effective aerosolization, and suitable particle size, it was concluded that butalbital was a compound suitable for aerosolization. It will be appreciated by the skilled artisan that the aerosol formulation may be modified to achieve a desired delivery of aerosolized butalbital.

TABLE 1

| | | | | Dose capture determinations | | | |
|---|---|---|---|---|---|---|---|
| Run Number | Formulation (Butalbital/Ascorbic Acid) | Form. Flow Rate (mg/sec) | Target Resistance (ohms) | Energy (J) | Air Flow Rate (L/min) | Dose Capture (%) | Degradation (%) |
| 1 | 0.2 | 5 | 0.590 | 68.22 | 0.5 | 115.24 | ND |
| 2 | 0.2 | 5 | 0.600 | 77.05 | 0.5 | 105.97 | ND |
| 3 | 0.2 | 5 | 0.610 | 84.43 | 0.5 | 109.56 | ND |
| 4 | 0.2 | 5 | 0.590 | 67.97 | 0.5 | 87.35 | ND |
| 5 | 0.2 | 5 | 0.600 | 68.30 | 0.5 | 71.92 | ND |
| 6 | 0.2 | 5 | 0.600 | 68.53 | 0.5 | 60.63 | ND |
| 7 | 0.2 | 5 | 0.600 | 73.38 | 0.5 | 66.39 | ND |
| 8 | 0.2 | 5 | 0.600 | 73.89 | 0.5 | 50.66 | ND |
| 9 | 0.2 | 5 | 0.600 | 73.69 | 0.5 | 73.30 | ND |
| 10 | 0.2/0.1 | 5 | 0.600 | 76.98[1] | 0.5 | 98.02 | 1.22 |
| 11 | 0.2/0.1 | 5 | 0.600 | 75.83[1] | 0.5 | 93.49 | 1.15 |
| 12 | 0.2/0.1 | 5 | 0.600 | 75.75[1] | 0.5 | 84.83 | 1.22 |
| 13 | 0.2/0.1 | 5 | 0.600 | 74.36[1] | 0.5 | 94.20 | 1.13 |
| 14 | 0.2/0.1 | 5 | 0.600 | 72.21[1] | 0.5 | 97.73 | 1.07 |

MP—mobile phase

ND—not determined

[1]Value based on an average of four actuations

TABLE 2

Particle size determinations.

| Run Number | Formulation (Butalbital/ Ascorbic Acid) | Flow Rate (mg/sec) | Target Resistance (ohms) | Energy (J) | MOUDI Number | MMAD (microns) | Material Balance (%) | Throat Deposition (%) | Wall Loss (%) |
|---|---|---|---|---|---|---|---|---|---|
| 1 | 0.2 | 5 | 0.600 | 75.06[1] | 374 | 0.538 | 90.74 | 1.60 | 5.86 |
| 2 | 0.2 | 5 | 0.600 | 74.77[1] | 375 | 0.510 | 81.87 | 2.65 | 5.13 |
| 3 | 0.2 | 5 | 0.600 | 75.38[1] | 376 | 0.461 | 68.71 | 2.28 | 5.10 |
| 4 | 0.2 | 5 | 0.600 | 76.22[1] | 377 | 0.607 | 96.41 | 2.22 | 3.53 |
| 5 | 0.2 | 5 | 0.600 | 75.33[1] | 378 | 0.624 | 96.16 | 2.42 | 4.43 |
| 6 | 0.2/0.1 | 5 | 0.600 | 73.02[1] | 379 | 0.341 | 107.24 | 1.90 | 2.36 |
| 7 | 0.2/0.1 | 5 | 0.600 | 73.85[1] | 380 | 0.377 | 93.81 | 1.47 | 1.95 |
| 8 | 0.2/0.1 | 5 | 0.600 | 73.84[1] | 381 | 0.344 | 94.19 | 2.98 | 4.57 |
| 9 | 0.2/0.1 | 5 | 0.600 | 74.36[1] | 382 | 0.390 | 102.42 | 3.17 | 2.33 |
| 10 | 0.2/0.1 | 5 | 0.600 | 72.21[1] | 383 | 0.368 | 88.95 | 6.83 | 2.44 |

MP—mobile phase
[1]Value based on an average of four actuations.

Example 2

Lorazepam Aerosol

An aerosol was generated using lorazepam (7-chloro-5-(2-chlorophenyl)-3-hydroxy-1,3-dihydro-2H-1, 4-benzodiazepin-2-one) dissolved in propylene glycol (PG).

Experiments were performed to determine if a chemically stable 0.5 μm lorazepam aerosol could be generated using a 28 gauge, 44 mm long steel capillary using a flow rate of 5 mg/second. The aerosol particle size was determined, the use and concentration of a stabilizer was evaluated, and the chemical stability of lorazepam in the generated aerosol was evaluated. Lorazepam was purchased from Sigma Aldrich Chemical Co. Propylene glycol was purchased from Dow Chemical Co.

Sham Determinations

Sham determinations were performed for each set of experiments to determine an "expected" amount of active per capillary aerosol generator (CAG). This was performed by running the equipment at a target resistance of 0.2 ohms, which pumped out the solution of lorazepam in PG as a liquid instead of an aerosol. This was collected on a Kimwipe which was placed into sample solvent and sonicated. This process was performed in triplicate. A 0.2% lorazepam solution in PG was prepared as the formulation.

Particle Size Determinations

Aerosol particle size was determined using the 10-stage MOUDI operated at 30L/minute. The sample foils were placed in beakers, 10 mL of sample solvent was added, and the beakers swirled thoroughly. For the USP throat, 10 mL of sample solvent was added and swirled thoroughly. Wall losses were assessed by washing the MOUDI walls with a Kimwipe dipped in mobile phase. The same 10 mL of mobile phase was used to wash the walls of all the stages.

Dose Capture and Degradation Determinations

Dose capture determinations were conducted (Table 3). In the initial runs 1-3, a material balance of intact lorazepam was not obtained. A proposed degradation peak (retention time of approximately 35 minutes) was observed in each of these experiments. Heating lorazepam to greater than 200 degrees Celsius resulted in rearrangement and a loss of water to produce a carboxaldehyde. To confirm the relationship of lorazepam to this product, lorazepam was placed in 1M HCl and stored at 50 degrees Celsius for 2 hours. The sample was neutralized with NaOH and the sample was analyzed using the HPLC method. The peak observed at 35 minutes in the dose capture experiments was observed in the acid induced degradation sample, indicating a relationship between lorazepam and this analyte. A second vehicle mixture of PG containing 10% water was prepared. Again, the degradation peak was observed.

Although the experiments showed a relatively high chemical degradation at higher resistance, and a lack of thermal stability, the skilled artisan will appreciate that the aerosol formulation may be modified to achieve a desired delivery of aerosolized lorazepam.

TABLE 3

Dose capture and degradation determinations.

| Run Number | Formulation (Lorazepam/ Water) | Form. Flow Rate (mg/sec) | Target Resistance (ohms) | Energy (J) | Air Flow Rate (L/min) | Dose Capture (%) |
|---|---|---|---|---|---|---|
| 1 | 0.2 | 5 | 0.580 | 57.8 | 0.5 | 53 |
| 2 | 0.2 | 5 | 0.590 | 72.2 | 0.5 | 41 |
| 3 | 0.2 | 5 | 0.600 | 80.9 | 0.5 | 17 |
| 4 | 0.2 | 5 | 0.570 | 41.1 | 0.5 | 76 |
| 5 | 0.2 | 5 | 0.585 | 66.8 | 0.5 | 50 |
| 6 | 0.2/10 | 5 | 0.580 | 71.8 | 0.5 | 50 |
| 7 | 0.2/10 | 5 | 0.590 | 82.5 | 0.5 | 23 |
| 8 | 0.2/10 | 5 | 0.600 | 96.3 | 0.5 | 13 |

Example 3

Ipratropium Aerosol

An aerosol was generated using ipratropium bromide (endo,syn)-(±)-3-(3-Hydroxy-1-oxo-2-phenylpropoxy)-8-methyl-8-(1-methylethyl)-8-azoniabicyclo[3.2.1]octane bromide) dissolved in propylene glycol (PG).

Experiments were performed to determine if a chemically stable 0.5 µm ipratropium bromide aerosol could be generated using a 28 gauge, 44 mm long steel capillary using a flow rate of 5 mg/second. The aerosol particle size was determined, the use and concentration of a stabilizer was evaluated, and the chemical stability of ipratropium bromide in the generated aerosol was evaluated. Ipratropium Bromide was purchased from Sigma Aldrich Chemical Co. Propylene glycol was purchased from Dow Chemical Co.

Forced Degradation Studies

Ipratropium bromide was subjected to heating with a differential scanning calorimeter. Conditions were optimized to produce thermal degradation products by heating to 300 degrees Celsius.

Sham Determinations

Sham determinations were performed for each set of experiments to determine an "expected" amount of active per capillary aerosol generator (CAG) activation. This was performed by running the equipment at a target resistance of 0.2 ohms, which pumped out the solution of ipratropium bromide in PG as a liquid instead of an aerosol. The result was collected on a Kimwipe which was placed into sample solvent and sonicated. This process was performed in triplicate. Ipratropium bromide was dissolved in PG at a concentration of approximately 0.2%.

Dose Capture and Degradation Determinations

Dose capture determinations were conducted (Table 4). Intact ipratropium bromide was calculated based upon prepared standards. The extent of degradation was evaluated by assuming that the degradation products had similar extinction coefficients as the parent at the wavelength of interest.

Dose Capture and Degradation Determinations

Experiments indicated that at the energy required to aerosolize ipratropium bromide in PG, the compound was degrading significantly. This was in the form of many proposed degradation products and confirmed by the very low recoveries (<20%) even at low resistance/temperature conditions.

Although the experiments showed a relatively high chemical degradation at higher resistance, and a lack of thermal stability, the skilled artisan will appreciate that the aerosol formulation may be modified to achieve a desired delivery of aerosolized ipratropium.

Example 4

Baclofen Aerosol

An aerosol was generated using baclofen (β-(Aminomethyl)-4-chlorobenzenepropanoic acid) dissolved in propylene glycol (PG).

Experiments were performed to determine if a chemically stable 0.5 cm baclofen aerosol could be generated using a 28 gauge, 44 mm long steel capillary using a flow rate of 5 mg/second. The aerosol particle size was determined, the use and concentration of a stabilizer was evaluated, and chemical stability of baclofen in the generated aerosol was evaluated. Baclofen was purchased from Sigma Aldrich Chemical Co.

Forced Degradation Studies

A dose capture experiment was conducted at a target resistance of 0.590 ohms to verify suspected degradation. A target resistance of 0.590 ohms was determined to be the lowest resistance which would aerosolize baclofen.

It will be appreciated by the skilled artisan that the aerosol formulation may be modified to achieve a desired delivery of aerosolized baclofen.

Example 5

Morphine Aerosol

An aerosol was generated using morphine (5α, 6α)-7,8-Didehydro-4,5-epoxy-17-methyl morphinan-3,6-diol) dissolved in propylene glycol (PG). Experiments were performed to determine if a chemically stable 0.5 µm morphine aerosol could be generated using a 28 gauge, 44 mm long steel capillary using a flow rate of 5 mg/second. A 0.2% morphine solution in PG was prepared as the formulation to be tested. The aerosol particle size was determined, the use and concentration of a stabilizer was evaluated, and chemical stability of morphine in the generated aerosol was evaluated. Morphine was obtained from Virginia Commonwealth University, Department of Medicinal Chemistry.

Forced Degradation Studies

Morphine was subjected to heating with a differential scanning calorimeter. The conditions produced total thermal degradation products by heating to 350 degrees Celsius.

Dose Capture and Degradation Determinations

Experiments indicated that an energy of greater than about 70 J was required to aerosolize morphine and minimize throat deposition. This was further refined to a target resistance of 0.600 ohms to provide an energy input of about 73 J. Using these parameters, an average of >90% of the morphine (runs 4-7 from Table 5) was aerosolized and collected. Run 8 provided a recovery of approximately 60%. This value is signifi-

TABLE 4

Dose capture determinations.

| Run Number | Formulation (Ipratropium) | Form. Flow Rate (mg/sec) | Target Resistance (ohms) | Energy (J) | Air Flow Rate (L/min) | Dose capture (%) | Percent Degradation |
|---|---|---|---|---|---|---|---|
| 1 | 0.2 | 5 | 0.59 | 68.36 | 0.5 | 19.61 | ND |
| 2 | 0.2 | 5 | 0.60 | 77.92 | 0.5 | 3.82 | ND |
| 3 | 0.2 | 5 | 0.61 | 86.27 | 0.5 | 3.77 | ND |

ND—not determined cantly less than that obtained from the other runs conducted at a target resistance of 0.600 ohms (Table 5 runs 4-7 and Table 6 runs 1-5). It is assumed that this run was compromised and is not included in further analysis of data. The average degradation of runs 4-7 was less than 1.2%. This was in the form of one proposed degradation product.

Particle Size Determinations

Dose capture experiments indicated that morphine in PG could be aerosolized and captured. After determining energy requirements for aerosolizing morphine, particle size determinations were performed (Table 6). At energies of approximately 73 J (runs 1-5), less than about 6% of the recovered morphine was found on the throat. These produced aerosols having an average mass median aerodynamic diameter of approximately 0.43 microns. The average recovery for these experiments exceeded 93%.

Based upon the reproducible effective aerosolization, and suitable particle size, it was concluded that morphine was a compound suitable for aerosolization. It will be appreciated by the skilled artisan that the aerosol formulation may be modified to achieve a desired delivery of aerosolized morphine.

Experiments were performed to determine if a chemically stable 0.5 μm scopolamine aerosol could be generated using a 28 gauge, 44 mm long steel capillary using a flow rate of 5 mg/second. The aerosol particle size was determined, the use and concentration of a stabilizer was evaluated, and chemical stability of scopolamine in the generated aerosol was evaluated.

Scopolamine was purchased from Spectrum Chemical Co, and propylene glycol was purchased from Dow Chemical Co.

Sham Determinations

Sham determinations were performed for each set of experiments to determine an "expected" amount of activity per capillary aerosol generator (CAG). This was performed by running the equipment at a target resistance of 0.2 ohms, which pumped out the solution of scopolamine in PG as a liquid instead of an aerosol. This was collected on a Kimwipe which was placed into sample solvent and sonicated. This process was performed in triplicate and was analyzed with other analytical samples. A 0.5% scopolamine solution in PG was prepared.

Dose Capture and Degradation Determinations

Dose capture determinations were conducted. The samples were collected in 10 mL of sample solvent, further diluted

TABLE 5

Dose capture determinations.

| Run Number | Formulation (Morphine) | Form. Flow Rate (mg/sec) | Target Resistance (ohms) | Energy (J) | Air Flow Rate (L/min) | Dose Capture (%) | Percent Degradation |
|---|---|---|---|---|---|---|---|
| 1 | 0.2 | 5 | 0.590 | 63.11[1] | 0.5 | 57.90 | ND |
| 2 | 0.2 | 5 | 0.600 | 76.04[1] | 0.5 | 129.3[2] | ND |
| 3 | 0.2 | 5 | 0.610 | 85.82[1] | 0.5 | 93.83 | ND |
| 4 | 0.2 | 5 | 0.600 | 75.28[1] | 0.5 | 100.29 | 0.47 |
| 5 | 0.2 | 5 | 0.600 | 76.12[1] | 0.5 | 92.78 | 2.53 |
| 6 | 0.2 | 5 | 0.600 | 76.39[1] | 0.5 | 91.28 | 0.71 |
| 7 | 0.2 | 5 | 0.600 | 73.39[1] | 0.5 | 82.26 | 0.80 |
| 8 | 0.2 | 5 | 0.600 | 73.59[1] | 0.5 | 59.48 | 1.18 |

MP—mobile phase
ND—not determined
[1]Value based on an average of four actuations.
[2]Suspected carry-over from previous run.

TABLE 6

Particle size determinations.

| Run Number | Formulation (Morphine) | Flow Rate (mg/sec) | Target Resistance (ohms) | Energy (J) | MOUDI Number | MMAD (microns) | Material Balance (%) | Throat Deposition (%) | Wall Losses (%) |
|---|---|---|---|---|---|---|---|---|---|
| 1 | 0.2 | 5 | 0.600 | 73.23[1] | 384 | 0.436 | 98.64 | 3.77 | 5.02 |
| 2 | 0.2 | 5 | 0.600 | 73.98[1] | 385 | 0.433 | 95.33 | 5.32 | 4.95 |
| 3 | 0.2 | 5 | 0.600 | 72.51[1] | 386 | 0.438 | 93.80 | 6.58 | 8.87 |
| 4 | 0.2 | 5 | 0.600 | 73.98[1] | 387 | 0.419 | 83.54 | 6.41 | 7.00 |
| 5 | 0.2 | 5 | 0.600 | 72.96[1] | 388 | 0.414 | 94.21 | 5.62 | 3.41 |

[1]Value based on an average of four actuations.

Example 6

Scopolamine Aerosol

An aerosol was generated using scopolamine (9-methyl-3-oxa-9-azatricyclo[3.3.1.0$^{2,4}$]non-7-yl tropate) dissolved in propylene glycol (PG) while conforming to the device constraints.

with 10 mL of sample solvent, and analyzed for scopolamine and degradation products. Intact scopolamine was calculated based upon prepared standards. The "amount" of degradation was evaluated by assuming that the degradation products had similar extinction coefficients as the parent at the wavelength of interest. This is a flawed assumption as greater than 100% material balance is obtained. This indicated that degradation was overestimated. However, the profiles provide evidence of target resistance (temperature) effects.

Particle Size Determinations

Aerosol particle size was determined using the 10-stage MOUDI operated at 30 L/min. This was performed for various heaters, target resistance, formulations, and formulation flow rates. The sample foils were placed in beakers, 10 mL of sample solvent was added, and the beakers swirled thoroughly. For the USP throat, 10 mL of sample solvent was added and swirled thoroughly. Wall losses were assessed by washing the MOUDI walls with a Kimwipe dipped in methanol. The same 10 mL of methanol was used to wash the walls of all the stages.

Dose Capture and Degradation Determinations

Initial runs represented method development of the collection of the condensation aerosol. In reviewing runs 4 and 7-18 (Table 7), it was hypothesized that there were two possible situations occurring. The first was that the scopolamine was not being completely aerosolized and the second was that there was significant carry-over within the capillary between runs. This was hypothesized due to the high variability between the runs making up the series of three reported and indicated as potential carry-over situations. For example, runs 10-12 and 16-18 had relative standard deviations (RSDs) of approximately 25%. In an attempt to minimize the possibility of carry-over within the capillary, the capillary was rinsed between each run with methanol beginning with run 19. After the capillary was cleaned between each run, dose capture experiments at a target resistance of 0.590 ohms showed no degradation peak but had poor recovery (28% and 32%, runs 19-21 and 23-25, respectively). As the resistance was increased to 0.595 ohms and 0.600 ohms the recovery increased to 65% and 62%, respectively, but a degradation peak was detected. In an attempt to prevent degradation ascorbic acid (AA) was added to the formulation. The formulation containing 0.5% SCOP and 0.1% ascorbic acid was aerosolized at 0.600 ohms. The recovery was 65% with very little change on the degradation profile. In comparing runs 23-25 with runs 32-34, the degradation was 18% and 19% respectively, based upon peak area.

Particle Size Determinations

Data was collected regarding aerosol particle size (Table 8). MOUDI 308 utilized a target resistance of 0.595 ohms. The recovery, compared to sham experiments, was 16%. Of the 16% recovered, approximately one third was recovered in each of the throat, impactor, and impactor walls. Due to the poor recovery very little emphasis was placed on the calculated aerosol particle size of 0.43 μm. MOUDI Number309 (Table 9) was performed at a target resistance of 0.585 ohms. However, only 5% of the expected material was recovered (all on the throat), which indicated a lack of aerosol production at this low resistance. Table 9 indicates the distribution of scopolamine throughout the particle sizing apparatus. The total scopolamine collected was determined by summing the amount of scopolamine found on three major sections: the USP throat ("throat"), in the "impactor" (impactor inlet, all stages, and filter), and walls ("wall loss"). The percentage found in each section was determined by dividing the amount found in the section by the total scopolamine collected. The "Material Balance" was determined by dividing the total scopolamine collected by the scopolamine collected in sham experiments.

Although the experiments showed a relatively high chemical degradation at higher resistance, and a lack of thermal stability, the skilled artisan will appreciate that the aerosol formulation may be modified to achieve a desired delivery of aerosolized scopolamine.

TABLE 7

Dose capture and degradation determinations.

| Run Number | Formulation (Scopolamine/Ascorbic Acid) | Form. Flow Rate (mg/sec) | Target Resistance (ohms) | Energy (J) | Air Flow Rate (L/min) | Dose Capture (%) |
|---|---|---|---|---|---|---|
| 1 | 0.5 | 5 | 0.595 | 87.7 | 0.5 | 60 |
| 2 | 0.5 | 5 | 0.595 | 86.6 | 0.5 | 60 |
| 3 | 0.5 | 5 | 0.595 | 84.3 | 0.5 | 66 |
| 4 | 0.5 | 5 | 0.620 | 113.0 | 0.5 | 90[1] |
| 5 | 0.5 | 5 | 0.620 | 117.2 | 0.5 | 32 |
| 6 | 0.5 | 5 | 0.620 | 116.4 | 0.5 | 28 |
| 7-9 | 0.5 | 5 | 0.585 | 67.5[2] | 0.5[2] | 17[1,2] |
| 10-12 | 0.5 | 5 | 0.590 | 73.1[2] | 0.5[2] | 83[1,2] |
| 13-15 | 0.5 | 5 | 0.600 | 83.5[2] | 0.5[2] | 111[1,2] |
| 16-18 | 0.5 | 5 | 0.610 | 94.0[2] | 0.5[2] | 77[1,2] |
| 19-21 | 0.5 | 5 | 0.590 | 68.4[2] | 0.5[2] | 28[2] |
| 22 | 0.5 | 5 | 0.600 | 83.6 | 0.5[2] | 59 |
| 23-25 | 0.5 | 5 | 0.600 | 81.6[2] | 0.5[2] | 62[2] |
| 26-28 | 0.5 | 5 | 0.590 | 72.0[2] | 0.5[2] | 33[2] |
| 29-31 | 0.5 | 5 | 0.595 | 78.1[2] | 0.5[2] | 65[2] |
| 32-34 | 0.5/0.1 | 5 | 0.600 | 78.4[2] | 0.5[2] | 65[2] |

[1]Potential carry-over situation
[2]Mean of 3 determinations
[3]Mean of 2 determinations
ND—not determined

TABLE 8

Particle size determinations.

| Run Number | Formulation (Scopolamine) | Flow Rate (mg/sec) | Target Resistance (ohms) | Energy (J) | MOUDI Number | MMAD (microns) | Material Balance (%) | Throat Deposition (%) |
|---|---|---|---|---|---|---|---|---|
| 1 | 0.5 | 5 | 0.595 | 72.1 | 308 | 0.43 | 16 | 35 |
| 2 | 0.5 | 5 | 0.585 | 67.2 | 309 | ND | 5 | 100 |

ND—not determined

TABLE 9

Scopolamine Distribution Within MOUDI Runs

| MOUDI Number | Throat Deposition (%)[4] | Impactor[5] Deposition (%)[4] | Wall Loss (%)[4] | Material Balance (%)[6] |
|---|---|---|---|---|
| 308 | 35 | 37 | 28 | 16 |
| 309 | 100 | 0 | ND | 5 |

[4]Percentage of total recovery in experiment.
[5]Percentage of total recovery in experiment found in "Inlet" through "Filter".
[6]Percentage of total recovery compared to sham experiment.
ND—Not determined The above-described exemplary modes of carrying out the invention are not intended to be limiting. It will be apparent to those of ordinary skill in the art that modifications thereto can be made without departure from the spirit and scope of the invention as set forth in the accompanying claims.

For instance, while a heated capillary tube has been described as the preferred construction of the capillary passage, the capillary passage can comprise one or more channels in a laminate having a heater arranged along the channel(s), multiple capillary tube arrangements, a passage having a heater located inside the passage, coaxial arrangements including an annular channel for fluid flow, or the like.

What is claimed is:

1. A method of generating an aerosol comprising: supplying a liquid aerosol formulation to a capillary-sized flow passage,
    heating the liquid aerosol formulation in the capillary-sized flow passage so as to volatilize a liquid component thereof and form a vapor which exits from an outlet of the capillary-sized flow passage, and
    contacting the vapor with a gaseous medium so as to form an aerosol,
    wherein the liquid aerosol formulation includes at least one thermally stable active ingredient selected from the group consisting of scopolamine, pharmaceutically acceptable salts and esters thereof.

2. The method of claim 1, wherein the gaseous medium comprises air, and the aerosol comprises propylene glycol-containing particles having an MMAD of less than 3 μm.

3. The method of claim 1, wherein the aerosol comprises scopolamine particles having an MMAD of less than 3 μm.

4. The method of claim 1, wherein the aerosol is formed in a mouthpiece of a handheld inhaler.

5. The method of claim 1, wherein the aerosol includes particles of the thermally stable active ingredient having an MMAD of 0.1 to 2.5 μm.

6. The method of claim 1, wherein the capillary-sized flow passage is heated by a resistance heater located in a handheld inhaler, the hand-held inhaler including a power supply and control electronics which controls supply of electrical power to the resistance heater as a function of a resistance target in a range of 0.5 to 1 ohm.

7. An aerosol generator comprising:
    a liquid supply providing a liquid aerosol formulation comprising at least one thermally stable active ingredient selected from the group consisting of scopolamine, pharmaceutically acceptable salts and esters thereof;
    a capillary-sized flow passage in fluid communication with the liquid aerosol formulation from the liquid supply; and
    a heater operable to heat the liquid aerosol formulation in at least a portion of the capillary-sized flow passage sufficiently to vaporize the liquid aerosol formulation and generate an aerosol containing the active ingredient.

8. The aerosol generator of claim 7, wherein the aerosol generator is a hand-held inhaler having a mouthpiece, wherein the capillary-sized flow passage has an outlet in fluid communication with an interior of the mouthpiece.

9. The aerosol generator of claim 7, wherein the heater is a resistance heater comprising a section of a metal capillary tube, and the capillary-sized flow passage comprises the interior of the metal capillary tube.

10. The aerosol generator of claim 7, wherein the aerosol generator is a hand-held inhaler having a power supply and control electronics which controls supply of electrical power to the heater as a function of a control parameter selected to achieve boiling of the liquid aerosol formulation in the capillary-sized flow passage.

11. The aerosol generator of claim 7, wherein the liquid supply comprises a reservoir containing the liquid aerosol formulation under a pressure of no greater than about atmospheric pressure.

* * * * *